United States Patent [19]

Walters et al.

[11] 4,190,055
[45] Feb. 26, 1980

[54] CIRCUIT FOR DETERMINING THE PARAMETER CONTROL STATES OF AN IMPLANTED PACER

[75] Inventors: Robert A. Walters, Pittsburgh; Russell E. Hirtz, Arnold, both of Pa.

[73] Assignee: ARCO Medical Products Company, Leechburg, Pa.

[21] Appl. No.: 812,571

[22] Filed: Jul. 5, 1977

[51] Int. Cl.² .............................................. A61N 1/00
[52] U.S. Cl. ............................................ 128/419 PT
[58] Field of Search .................. 128/419 PG, 419 PT

[56] References Cited

U.S. PATENT DOCUMENTS

| | | | |
|---|---|---|---|
| 3,805,796 | 4/1974 | Terry, Jr. et al. | 128/419 PG |
| 3,833,005 | 9/1974 | Wingrove | 128/419 PG |
| 3,841,336 | 10/1974 | Daynard | 128/419 PT |
| 3,945,387 | 3/1976 | Adams | 128/419 PG |
| 4,049,004 | 9/1977 | Walters | 128/419 PG |

*Primary Examiner*—William E. Kamm
*Attorney, Agent, or Firm*—John C. Martin, Jr.

[57] ABSTRACT

A circuit for indicating at a remote location the control states of a fully implantable heart pacer includes a parallel to serial converter which receives the control states from a register which controls the parameters of the associated pacer. When the pacer is switched to an asynchronous or to a magnetic mode, the data is shifted through the parallel to serial converter. A delay is added between pulses when a particular logic state appears, and no delay is added if the complement of that logic state appears. The parameters can therefore be determined externally by observing the successive periods between stimulation pulses in the asynchronous or magnetic mode of the pacer.

7 Claims, 2 Drawing Figures

CIRCUIT FOR DETERMINING THE PARAMETER CONTROL STATES OF AN IMPLANTED PACER

BACKGROUND OF THE INVENTION

1. Field of the Invention

This invention relates to improvements in heart pacers, and more particularly to improvements in heart pacers of the type which are externally programmable or controllable by digital circuitry to exhibit variable operating parameters, and, still more particularly, to circuit means for remotely indicating the digital states controlling the parameters of an implantable heart pacer.

2. Description of the Prior Art

For some time, efforts have been made to provide a fully implantable heart pacer of which selected operating parameters can be externally controlled after the pacer has been implanted into the body of a patient. Parameters of interest may include the stimulation pulse amplitude, width, and rate, the refractory period, the sensitivity to naturally occurring heart pulses, the mode, i.e., asynchronous, synchronous, demand and so forth.

Typical heart pacers having such variable parameters are shown in U.S. Pat. Nos. 3,805,796 and 3,833,005. In addition, patent application Ser. No. 663,372 filed Mar. 3, 1976 by Robert A. Walters, and assigned to the assignee of the present invention discloses a heart pacer having variable operating parameters which are controlled by digital circuitry responsive to externally applied magnetic pulses. Said patent application Ser. No. 663,372 has been allowed, and is incorporated herein by reference.

In the circuits of the prior art, when a change in the stimulation pulse rate is made, the change is usually readily observable upon an electrocardiographic device connected to the patient. However, many of the other parameters which can now be externally controlled such as the sensitivity of the pacer, the refractory period of the pacer, and so forth, are not so readily observable. In fact, confirmation of the programmed change in the pacer may be impossible without the actual removal of the pacer from the patient. In addition, as the number of parameters which can be changed in a single pacer increases, the number of combinations of controlled data becomes cumbersomely large to confirm the change of all but the most important parameters. To illustrate, for example, if a pacer has eight selectable stimulation rates, two widths, four amplitudes, two modes, two refractory periods and four sensitivities, then there are 1,024 combinations which can be programmed. Consequently, what is needed is a means for simply determining or confirming that an implanted heart pacer has been properly programmed.

SUMMARY OF THE INVENTION

In light of the above, it is therefore an object of the invention to provide a circuit for externally or remotely indicating the digital data or states by which the parameters of a fully implantable heart pacer are controlled.

It is another object of the invention to provide such indicating circuit which can be utilized in conjunction with most existing heart pacer circuits of the type which provide for parameter control by digital circuit means, without requiring modification of the existing pacer or its control circuits.

It is another object of the invention to provide such indicating circuit which can be used conveniently in conjunction with an asynchronous or magnetic mode of an implanted pacer.

It is still another object of the invention to provide such indicating circuit which can disclose operating parameters of the heart pacer which are not normally observable on ordinary electrocardiographic systems, such as the refractory period and sensitivity of the pacer.

These and other objects, features, and advantages will become apparent to those skilled in the art from the following detailed description when read in conjunction with the accompanying drawings and appended claims.

BRIEF DESCRIPTION OF THE DRAWING

The invention is illustrated in the accompanying drawing wherein.

DETAILED DESCRIPTION OF THE PREFERRED EMBODIMENTS

Figure 1:
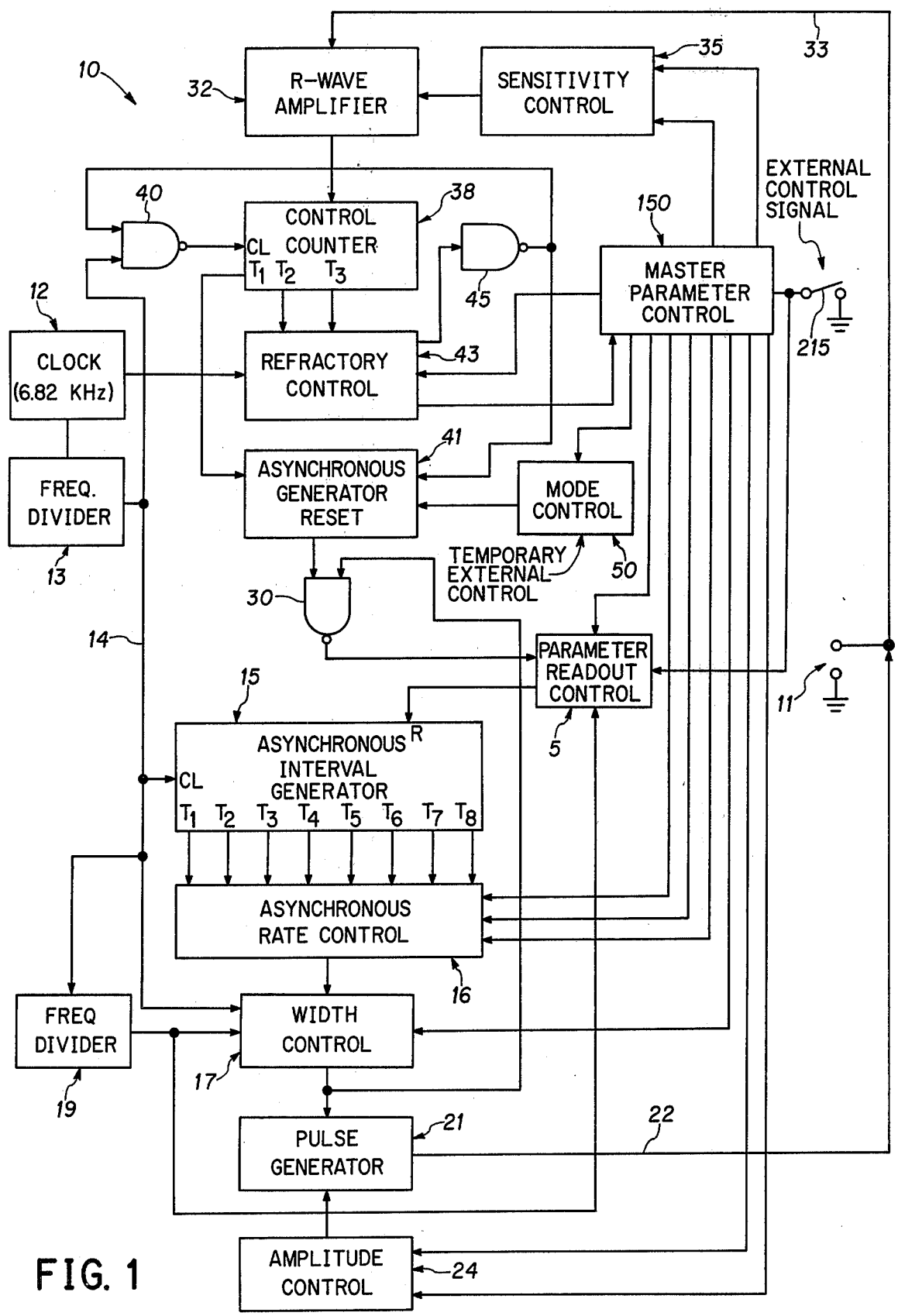
FIG. 1 is a box diagram of a heart pacer and digital control circuit for controlling the operating parameters thereof including the parameter readout control in accordance with the invention.

As shown in FIG. 1, the parameter readout control circuit 5 is used in conjunction with a heart pacer 10 of the type described in said above referenced patent application Ser. No. 663,372, filed Mar. 3, 1976, which, as mentioned, is incorporated herein by reference. The heart pacer 10 includes a pulse generator 21 for delivering heart stimulation pulses upon an output line 22 to terminals 11, which can be connected to appropriate electrodes (not shown) for connection to a patient's heart by any well known manner. The parameters of the pulse generator 21 are controlled by a digital parameter control circuit 16. The digital parameter control circuit receives digital clock pulses at various frequencies from a clock source 12 at a fundamental clock frequency, from a frequency divider 13 at a first divided frequency, and from a frequency divider 19 at a second divided frequency. The rate of heart stimulation pulses produced is controlled by an asynchronous interval generator 15 which receives clock pulses from the first divided clock pulse source, the frequency divider 13 upon line 14. The asynchronous interval generator 15 produces a number of outputs at various times indicated by outputs $T_1-T_8$ to an asynchronous rate control circuit 16. The asynchronous rate control circuit 16 selects one of the outputs $T_1-T_8$ of the asynchronous interval generator 15 in accordance with parameter states contained in a control register 62 (shown in FIG. 2) of a master parameter control circuit 150, the details of which are shown in said patent application Ser. No. 663,372. The output of the asynchronous rate control 16 is applied to a width control circuit 17 to produce a controlled pulse of selectable width, as determined by a corresponding state in the control register 62 of the master parameter control circuit 150. Thus, the width control 17 selects from the first divided clock frequency pulses upon line 14 or a second divided clock frequency pulses produced by the frequency divider 19, both of which are applied as inputs to the width control circuit 17. The output of the width control circuit 17, therefore, is applied to the pulse generator 21 to cause it to produce output pulses at the rate selected from the asynchronous interval generator 15 at a width selected by the width control circuit 17. In addition, the output of the width control circuit 17 is applied to reset the asynchronous interval generator 15 by a NAND gate 30, and the parameter readout control circuit 5. The readout control circuit 5 causes a resetting of the asynchronous interval counter 15 either immediately or after a delayed time, in accordance with the mode of the pacer and the various states in the control register 62 of the master parameter control circuit 150, all as below described in detail, to begin the pulse initiation timing anew.

Also, the amplitude of the pulse generated by the pulse generator 21 is controlled by the amplitude control circuit 24, which also is responsive to the states in the master parameter control register 62 of the master parameter control circuit 150.

The circuit thus described is operable as an asynchronous heart pacer, to produce pulses for delivery to stimulate the patient's heart at constant selectable times with a selectable amplitude and width. To enable the pacer thus described to operate in a demand mode, pulses appearing at the electrode connection terminals 11 are conducted upon a line 33 to an R-wave amplifier 32 for delivery to a refractory control circuit, as below described. The sensitivity of the R-wave amplifier 32 is controlled by a sensitivity control circuit 34 which, in turn, is controlled by the master parameter control circuit 150.

The output from the R-wave amplifier 32 is conducted to a control counter circuit 38, which has three outputs denoted $T_1$-$T_3$. The outputs $T_2$ and $T_3$ are connected to a refractory control circuit 43, which selects between the two control counter outputs in accordance with the master parameter control circuit 150. Briefly, when the selected output of the control counter 38 occurs, it is passed to a NAND gate 45 connected as an inverter for delivery to an input of NAND gate 40, the output of which is connected to the clock terminal of the control counter 38. The first divided clock pulses upon the line 14 are connected to the other terminal of the NAND gate 40. Thus, when the output of the control counter 38 occurs, the clock pulses are disabled by the gate 40 from further clocking of the control counter 38. Thereafter, upon the reception and detection of a pulse by the R-wave amplifier 32, the control counter 38 is reset and enabled to again begin counting. Upon reaching the first count, the output $T_1$ occurs, thereby activating the asynchronous generator reset circuit 41, previously enabled by the output from the gate 45, to be passed through the NAND gate 30 for delivery to the parameter readout control circuit 5. The parameter readout control circuit 5 then causes the resetting of the asynchronous interval generator 15. The circuit thus described is a demand circuit, which produces heart stimulation pulses upon the terminals 11 only in the absence of naturally occurring heart pulses, in proper time step therewith, in a manner known in the art.

To enable checking of the operation of the pacer 10, a magnetically actuated reed switch 215 is provided, the activation of which, in addition to providing means for transmitting parameter control data to the master parameter control circuit 150, causes the heart pacer 10 to operate in an asynchronous mode, also typically referred to as a magnetic mode, in which the naturally occurring heart wave detecting circuitry is disabled, allowing the asynchronous interval generator 15 to operate continuously without being reset at intermediate times. (This operation mode can additionally be selected as a normal operating parameter, controlled again by the master parameter control circuit 150 by a mode control circuit 50.)

Figure 2:
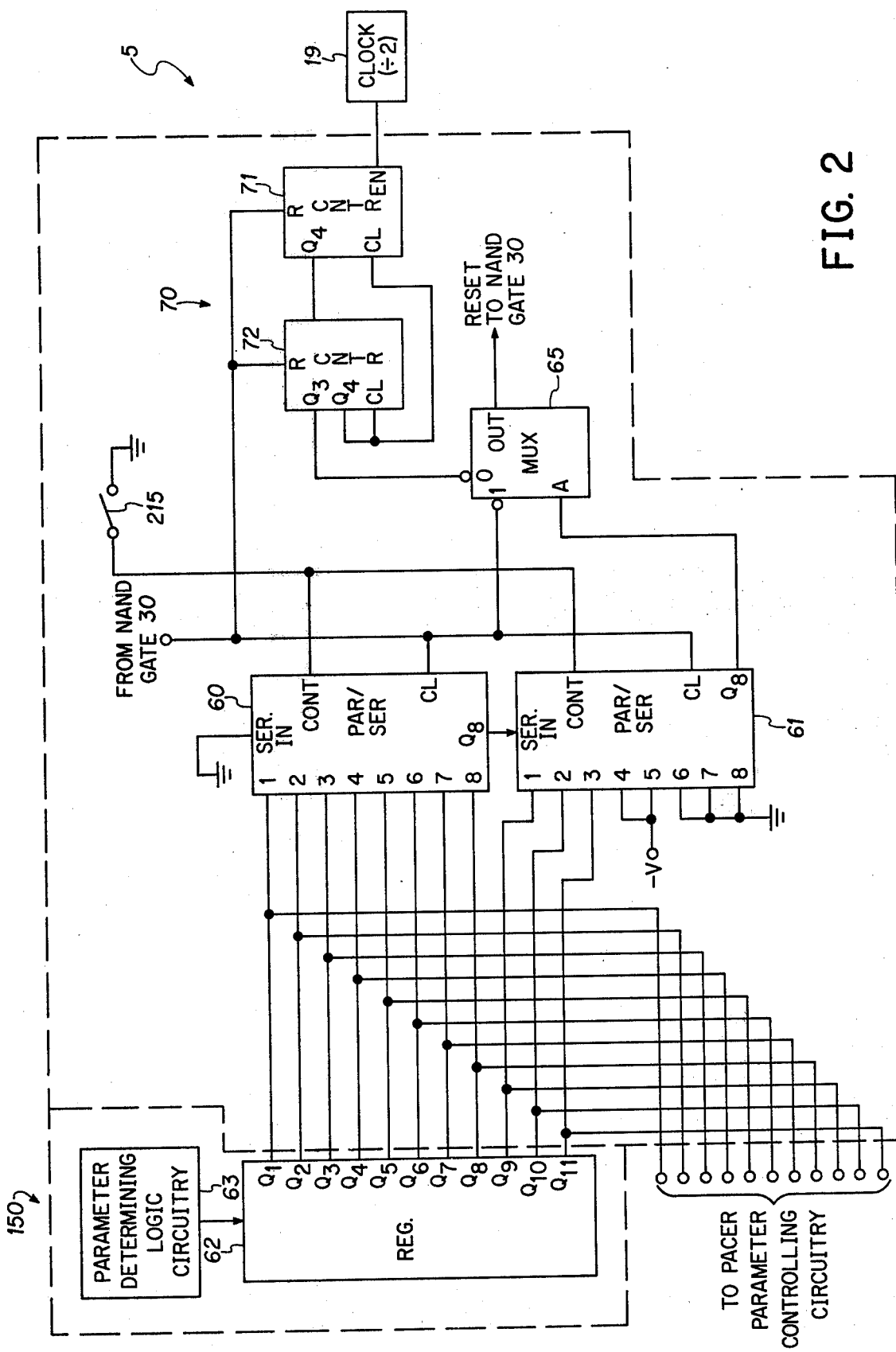
FIG. 2 is a schematic diagram of the parameter readout control used in the heart pacer and control circuit of FIG. 1.

To indicate the states in the register of the master parameter control circuit 150 which control the various parameters, above described, the parameter readout control circuit 5 is provided, and is described now with reference to FIG. 2. As shown, the parameter readout control circuit 5 includes two eight stage parallel-to-serial shift registers 60 and 61 connected to receive the states of the parameter determining register 62 of the master parameter control circuit 150. (The various output states $Q_1$-$Q_{11}$ of the register 62 are controlled by parameter determining logic circuitry 63, as described in detail in said patent application Ser. No. 663,372.)

The respective parallel-serial control terminals of the shift registers 60 and 61 are connected to the magnetically actuatable reed switch 215. The serial input terminal of the shift register 60 is connected to ground or a logic high state, and the serial input of the shift register 61 is connected to the $Q_8$ output terminal of the shift register 60. The output from the two shift registers, therefore, serially appears at the output terminal $Q_8$ of the shift register 61. The clock terminals of the shift registers 60 and 61 are connected to be clocked by the occurrence of the pulse from the pulse generator 21 (see FIG. 1). In the embodiment illustrated, the clock pulse is derived at the output of the NAND gate 30, having its input derived from the output of the width control circuit 17. Thus, when the pulse generator 21 is signalled to pulse, a clock pulse is delivered to clock the respective parallel-to-serial shift registers 60 and 61.

It can therefore be seen that in operation upon the closure of the reed switch 215, the data in the latch or register 62 is jammed into the inputs of the parallel-to-serial shift registers 60 and 61, and upon the subsequent production of stimulation pulses by the pacer (or by a direction to the pulse generator 21 to produce a stimulation pulse), the data is shifted in synchronizm therewith in a serial fashion out of the registers upon the $Q_8$ output terminal of the parallel-to-serial converter 61. It should be noted that the first three data positions of the parallel-to-serial converter 61 (numbers 6, 7, and 8) are connected to ground or a logic high state, and the following two inputs (numbers 4 and 5) are connected to a logic low state, or $-V$. Thus, the first five data bits shifted from the registers 60 and 61 will be 111000, thereby providing a unique signal indicating that the parameter control data follows.

The output $Q_8$ of the parallel-to-serial converter 61 is connected to the "A" control terminal of a multiplexer 65. The "1" terminal of the multiplexer is connected to receive the resetting pulse from the NAND gate 30, and the "0" terminal is connected to receive the output from a digital one shot circuit 70. The output of the multiplexer 65 is connected to reset the asynchronous interval generator 15, via the NAND gate 30, as shown in FIG. 1.

The digital one shot circuit 70, in the embodiment illustrated, includes two counters 71 and 72. The counter 71 is connected to receive clock pulses from the output of the frequency divider 19 at its enable terminal. The counter 72 receives its enabling pulses from the $Q_4$ output of the counter 71, to produce outputs upon its $Q_3$ and $Q_4$ terminals. The $Q_4$ output terminal of the counter 72 is connected to the clock terminals of both counters 71 and 72. Additionally, the reset terminals of both counters are connected to the output of the NAND gate 30, to be reset upon the production of a heart stimulation pulse.

The counters 71 and 72 are of the type which advance in count upon a state change appearing on the enable line when the clock terminal is at a logic low or zero state, and which produce no change or count when the clock terminal is in a high or one state. Thus, in operation, after being reset, the counters 71 and 72 commence counting clock pulses from the clock frequency divider 19 to produce an output upon the $Q_3$ terminal of the counter 72 after approximately 88 milliseconds for delivery to the zero input of the multiplex circuit 65. After the output pulse upon the output terminal $Q_3$ is produced, as the counters 71 and 72 continue to be clocked, the output terminal $Q_4$ of the counter 74 changes state, thereby applying a logic high state to the clock terminals of both counters 71 and 72, disabling their further count.

The effect of the digital one shot circuit 70, when selected by the multiplexer 65, is to add a delay to the effective time of the reset pulse produced by the stimulation pulse of the pacer (or in the case of the preferred embodiment illustrated, in response to the pulse produced from the width control circuit 17 to the pulse generator 21 to produce a stimulation pulse).

It can therefore be seen that as the data within the parallel-to-serial registers 60 and 61 is shifted from them upon the $Q_8$ terminal of the parallel-to-serial converter 61, either the zero or one input terminal of the multiplexer 65 will be selected, depending upon whether the state shifted from the parallel-to-serial converter 61 is a logic low, or zero, or logic high, or one, state. If the 0 input of the multiplexer 65 is selected when a low state is applied to the A control terminal and the 1 input is selected when a high state is applied to the A terminal, it can be seen that as the data is shifted through the parallel-to-serial converters 60 and 61, the output upon the output line 74 to the reset terminal of the asynchronous interval generator 15 will be either directly applied, in usual fashion or delayed by the delay produced by the digital one shot circuit 70, in accordance with the master parameter control states.

The effect of this delay can be externally observed by observing the patient's pulse rate immediately after the pacer is switched to its magnetic or asynchronous mode by operation of the magnetic reed switch 215. Thus, the stimulation pulse period between adjacent pulses will be either that of the selected asynchronous rate or that of the asynchronous rate plus the delay added by the digital one shot, depending upon whether the data within the master parameter control register 62 is a logic low or high state. The selectively added delay, corresponding in location to a correspondingly located respective logic state of the control register, effectively pulse position modulates the stimulation pulses produced by the pacer. The pulse stream therefore can be decoded to indicate the logic states originally in the control register 62.

To insure that the pacer produces pulses at a proper asynchronous rate after the initial few pulses have been produced, the serial input of the parallel-to-serial converter 60 is connected to a logic high state, to thereby cause to be selected the 1 input of the multiplexer 65 after the data of the master parameter control register 62 has been shifted completely through the parallel-to-serial converters 60 and 61.

It should also be noted that although the digital one shot 70 in the embodiment illustrated has been fabricated to produce a delay of approximately 88 milliseconds, any delay can be selected, so long as it produces a discernable difference in the periods of the stimulation pulses produced by the pacer.

In addition, although the circuit has been shown to add a delay to pulses corresponding in position to the relative positions of logic high or one states in the control register 62, it can easily be constructed to add a delay corresponding to logic low or zero states.

Although the invention has been described and illustrated with a certain degree of particularity, it is understood that numerous changes in the combination and arrangement of parts may be resorted to by those skilled in the art without departing from the spirit and scope of the invention as hereinafter claimed.

We claim:

1. In combination with a heart pacer of the type in which operating parameters of the pacer are controlled by logic states established in a register connected to parameter controlling circuitry and having an externally selectable asynchronous mode in which said pacer produces asynchronously occurring stimulation pulses, means for producing serial logic states corresponding, in order, to each of said established logic states, and a delay circuit for selectively adding, in correspondence with the logic state of a respective one of said serial logic states, a delay between successive asynchronous stimulation pulses to provide an observable indication of said established logic states when said asynchronous mode of said pacer is selected.

2. A circuit for use with a fully implantable heart pacer to remotely indicate the states of a digital register operatively associated with the pacer to control the pacer parameters, comprising:

means to produce a selected operating mode of the pacer, and means activated by said mode selecting means to pulse position modulate a number of pacer stimulation pulses in sequence with each of the states of said register.

3. The circuit of claim 2 wherein said means to produce a selected operating mode of the pacer is a magnetically actuatable reed switch connected to said pacer to produce an asynchronous operating mode.

4. The circuit of claim 2 wherein said means to pulse position modulate a number of stimulation pulses comprises:

a shift register connected to receive the states of said digital register, clocked in conjunction with the pacer stimulation pulses to serially output the received states, and means for detecting the received states serially outputted from said shift register to delay a next occurring stimulation pulse upon detecting a preselected state.

5. A circuit for connection to an implantable heart pacer having an output pulse for delivery to stimulate a user's heart, and having variable parameters controlled by externally changeable data in a parameter data containing register, to externally indicate the data in said register, comprising:

externally actuatable means for producing an asynchronous mode of operation of said pacer, shift register means connected to the parameter data containing register and said externally actuatable mode producing means to receive the data in said parameter data containing register when said externally actuatable means produces the asynchronous mode, said shift register means being clocked by the output pulse of said pacer to serially produce the parameter controlling data at a shift register output, and means for controlling the rate of each pacer output pulse in accordance with the serial output of said shift register means to produce a first interpulse period corresponding to a zero and a second interpulse period corresponding to a one, of each of said shift register means output, whereby the periods between successive stimulation pulses of said pacer are indicative of the data in said parameter data containing register.

6. The circuit of claim 5 wherein said externally actuatable means for producing an asynchronous mode of operation comprises a magnetically actuatable reed switch.

7. The circuit of claim 5 wherein said means for controlling the rate of each pacer output pulse comprises delay means responsive to the serial outputs of said shift register to delay the next occurring pacer output pulse a predetermined time in response to the occurrence of a zero.

* * * * *